(12) United States Patent
Weinstein et al.

(10) Patent No.: US 9,649,108 B2
(45) Date of Patent: May 16, 2017

(54) ORTHOPEDIC BONE STAPLE WITH POLYAXIAL COMPRESSION CAPABILITY

(71) Applicant: ORTHOVESTMENTS, LLC, Marietta, GA (US)

(72) Inventors: Robert Brian Weinstein, Atlanta, GA (US); Samuel Alexander White, Atlanta, GA (US)

(73) Assignee: ORTHOVESTMENTS, LLC, Marietta, GA (US)

( * ) Notice: Subject to any disclaimer, the term of this patent is extended or adjusted under 35 U.S.C. 154(b) by 0 days.

(21) Appl. No.: 14/945,887

(22) Filed: Nov. 19, 2015

(65) Prior Publication Data

US 2016/0242771 A1 Aug. 25, 2016

Related U.S. Application Data

(60) Provisional application No. 62/119,830, filed on Feb. 24, 2015.

(51) Int. Cl.

| | |
|---|---|
| *A61B 17/84* | (2006.01) |
| *A61B 17/064* | (2006.01) |
| *A61B 17/86* | (2006.01) |
| *A61B 17/88* | (2006.01) |
| *A61B 17/00* | (2006.01) |
| *A61B 90/00* | (2016.01) |

(52) U.S. Cl.
CPC ........ *A61B 17/0642* (2013.01); *A61B 17/842* (2013.01); *A61B 17/86* (2013.01); *A61B 17/88* (2013.01); *A61B 2017/00867* (2013.01); *A61B 2090/061* (2016.02)

(58) Field of Classification Search
CPC ........ A61B 17/0642; A61B 2017/0641; A61B 17/064
USPC .......................................................... 606/75
See application file for complete search history.

(56) References Cited

U.S. PATENT DOCUMENTS

| | | | | |
|---|---|---|---|---|
| 3,212,819 | A | * | 10/1965 | Churchill ............... B24D 13/08 15/179 |
| 4,592,346 | A | * | 6/1986 | Jurgutis ............. A61B 17/0642 411/457 |
| 4,793,335 | A | | 12/1988 | Frey et al. |

(Continued)

FOREIGN PATENT DOCUMENTS

| | | |
|---|---|---|
| EP | 1070482 A2 | 1/2001 |
| EP | 2361571 A2 | 8/2011 |

(Continued)

OTHER PUBLICATIONS

International Search Report & Written Opinion for PCT/US2016/019187; Apr. 20, 2016; 13 pgs.

*Primary Examiner* — Zade Coley
(74) *Attorney, Agent, or Firm* — Gardner Groff Greenwald & Villanueva, PC

(57) ABSTRACT

A bone fixation device or bone staple includes a crown portion, an engagement portion, and an outer rim generally defined between the crown portion and the engagement portion. The engagement portion includes a plurality of legs extending from the outer rim in a direction away from the crown portion. The plurality of legs are generally radially disposed and evenly spaced apart around the outer rim. The legs are beveled to provide a compressive effect to the bone when the staple is inserted into the bone.

12 Claims, 15 Drawing Sheets

(56) References Cited

U.S. PATENT DOCUMENTS

| | | | | |
|---|---|---|---|---|
| 4,960,420 A * | 10/1990 | Goble | | A61B 17/0642 411/457 |
| 4,988,351 A * | 1/1991 | Paulos | | A61B 17/8625 606/232 |
| 5,250,058 A | 10/1993 | Miller et al. | | |
| 5,314,427 A * | 5/1994 | Goble | | A61B 17/0642 411/457 |
| 5,352,229 A * | 10/1994 | Goble | | A61B 17/0642 606/220 |
| 5,779,707 A * | 7/1998 | Bertholet | | A61B 17/8004 606/301 |
| 5,931,869 A * | 8/1999 | Boucher | | A61B 17/0642 128/898 |
| 5,947,969 A * | 9/1999 | Errico | | A61B 17/7032 606/308 |
| 6,328,743 B2 * | 12/2001 | Lerch | | A61B 17/84 606/215 |
| 6,348,064 B1 | 2/2002 | Kanner | | |
| 6,482,232 B1 * | 11/2002 | Boucher | | A61B 17/0642 606/309 |
| 6,524,311 B2 | 2/2003 | Gaines, Jr. | | |
| 6,569,186 B1 * | 5/2003 | Winters | | A61B 17/0401 606/104 |
| 6,712,822 B2 | 3/2004 | Re et al. | | |
| 7,481,830 B2 * | 1/2009 | Wall | | A61B 17/7059 606/286 |
| 8,021,389 B2 | 9/2011 | Molz, IV | | |
| 8,062,297 B2 | 11/2011 | Faillace et al. | | |
| 8,529,609 B2 * | 9/2013 | Helgerson | | A61B 17/7064 606/247 |
| 8,623,020 B2 | 1/2014 | Kim et al. | | |
| 8,900,281 B2 | 12/2014 | Reisberg | | |
| 2012/0130374 A1 | 5/2012 | Bouduban et al. | | |
| 2013/0110183 A1 * | 5/2013 | Duggal | | A61B 17/7064 606/328 |
| 2015/0230839 A1 * | 8/2015 | Riccione | | A61B 17/8014 606/297 |

FOREIGN PATENT DOCUMENTS

| | | |
|---|---|---|
| FR | 2715290 A1 | 7/1995 |
| FR | 2980966 A1 | 4/2013 |
| FR | 2991569 A1 | 12/2013 |
| WO | 2006122194 A1 | 11/2006 |

* cited by examiner

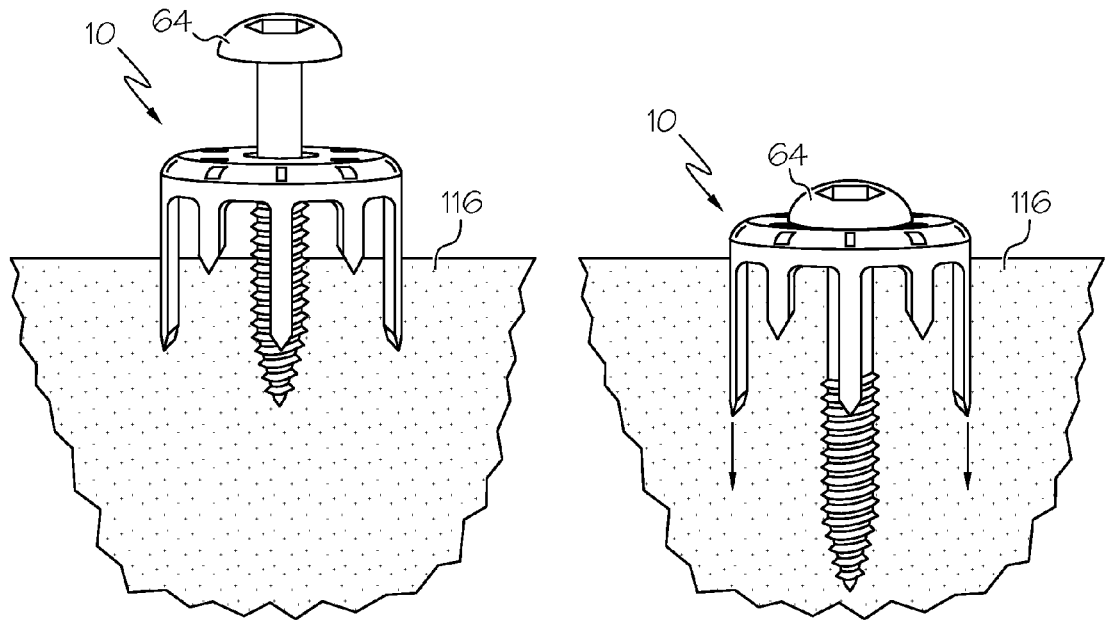
FIG. 8
FIG. 9
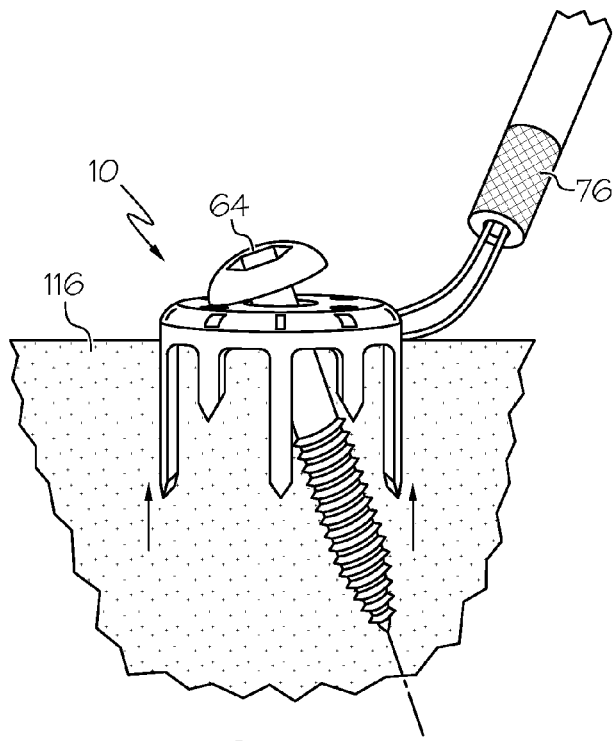
FIG. 10

ORTHOPEDIC BONE STAPLE WITH POLYAXIAL COMPRESSION CAPABILITY

CROSS-REFERENCE TO RELATED APPLICATION

This application claims the benefit of U.S. Provisional Patent Application Ser. No. 62/119,830 filed Feb. 24, 2015, which is hereby incorporated herein by reference.

TECHNICAL FIELD

The present invention relates generally to the field of orthopedic surgery including methods and devices for joining and compression of bone tissue in orthopedic surgical procedures, and more particularly to devices and methods enabling joining and compression of bone tissue in one or multiple directions simultaneously.

BACKGROUND

It is common in the field of orthopedic surgery to perform operations involving bones where the procedural demands require close approximation of one bone to another. For example, procedures in which a joint is removed and two bones are surgically fused together requires first the apposition of the bones and then continued apposition throughout the phases of bone healing. For this purpose, a variety of devices are available to the surgeon such as pins, wires, screws, plates and staples. The surgeon approaches the condition with this variety in mind and generally will choose the device with the best profile for completing the task. For example, when strict axial compression of a long bone fracture is desired, a bone screw is typically selected. For very small bone fragments or avulsion type injuries, wires and pins are typically selected. And when the angle of approach to approximation is too obtuse for either screws or wires, such as with two flat bones ends, a staple is often selected to maintain bone alignment.

A variety of bone staples have been developed for use in various surgical procedures. Bone staples are commonly configured as a U-shaped member, having two legs and a central web or crown. Bone staples are available in variations of size, material, and insertional tools. For size variations, larger format staples are used for larger bones, and likewise smaller staple sizes are used for smaller bones. As staple width or height dimension increases or decreases respectively the leg and crown girth may be increased or decreased relative to the stability of the staple when implanted (e.g. larger girth crown for larger staples). Staples may also be made from different materials, including stainless steel, titanium, plastics, and shape-memory alloys such as Nitinol. Insertional tools vary among staple manufacturers but generally are specialized to implant or explant a particular design.

Some staples are delivered to the surgeon in a "pre-bent" configuration, for example, when the staples are inserted while bent and upon removal of the insertion tool revert to a pre-bent shape. Variations of staples also include modifications such as grooves on the legs, spikes on the crown, step changes on the crown, and grooves or hooks for insertion tools. Grooves are placed on the legs on their interior or exterior in order to enhance resistance to the staple pulling out of the bone tissue, which would be counter to the desired effect of the staple. This problem is fairly common and one or both loose legs can lead to failure of an implant. Spikes on the undersurface of the crown assist with maintenance of the staple against the substrate and stability of the overall construct. Step changes on the crown can occur co-axially with the legs or in the horizontal plane. Co-axial step changes in the crown account for particular bone procedures where one bone may sit higher or lower than another while they are opposed. This allows the staple to seat flush with the bone surfaces underneath. Step changes on the horizontal plane have been developed to aid in the compressive effort of insertional tools when they are used to 'pull' the legs of the staple together.

Compression of bone ends through the healing process is beneficial in some applications. For some applications, staples do not provide compression and serve as splintage of bone ends. In other applications, static compression is provided when one leg of a staple is pulled towards the other, either due to a shape memory effect of certain metals, the geometry change of prying the crown apart with certain tools, or by exploiting a pre-bent effect that some instrumentation can maintain until the staple is inserted. Regardless of the methods demonstrated in the current state of the art, the compression achieved at the time of insertion is static and does not increase over time or with deleterious distractive forces at bone ends. In addition, current compressive staples are designed to create axial compression, where one leg compresses towards the other along an axis created by the crown. Because demands of surgical operations often vary, axial compression may not be desired based on the position of the staple when it is inserted. For example, oblique positioning of a compression staple across a linear fusion site will introduce shear, a deleterious force when attempting to compress bone ends symmetrically.

There are several principles followed for insertion of a bone staple that are common to all of the variants. First the size must be appropriate. Too small a staple, and the legs can violate the fusion site, or the device may be inadequate to resist the distractive forces on the bone ends. Second, any 'pilot' holes or pre drilling for the staple legs must be sufficiently small to avoid removal or displacement of bone required for the staple to seat securely in the bone. Loss of bone purchase can lead to loosening or inability to use this fixation method. Third, the staple legs should typically sit directly perpendicular to the fusion or fracture line since a deleterious shear force will be introduced if the implant is placed obliquely. This principle is particularly important when using a compressive staple. Fourth, the staple should have some obliquity to insertion of the legs, since discrete or strict axial applications are less effective at resistance to pulling out of the bone.

It has now been recognized that needs exist for improved bone staples, improved methods of use of bone staples, and improved staple implantation devices and procedures. It is to the provision of improved bone staples, methods and implantation devices and procedures meeting these and other needs that the present invention is primarily directed.

SUMMARY

Example embodiments of the present invention relate to a bone fixation device or bone staple for securing two bone ends together in approximation, and enabling poly-axial compression ability such that compression of the bones can be achieved in multiple directions simultaneously.

In one aspect, the present invention relates to a bone staple including a crown portion and an engagement portion. The crown portion can include a generally circular body including a top surface and a bottom surface generally opposite thereto, the circular body having a central opening and one or more adjacent peripheral openings generally positioned adjacent or around the central opening. The engagement portion generally extends from the crown portion and can include a plurality of legs of alternating different lengths generally radially disposed around the perimeter of the circular body. In example forms, at least one of the legs includes one or more bevels formed at an end portion thereof, and wherein the one or more obliquely inclined bevels are configured so that the legs generally diverge from a central axis that is axially aligned with the central opening of the crown portion when inserted into a bone.

In example forms, at least one of the legs has a first length and at least another of the legs has a different second length. According to one form, the first and second lengths of the legs have a ratio L1:L2 of about 2:1. According to example forms, the engagement portion has about ten legs extending therefrom, wherein about five of the legs have a first length and wherein about five of the legs have a second length, and wherein the legs alternate in length between the first length and the second length around the perimeter of the crown portion. Each of the legs includes an outer surface, an inner surface, side surfaces, and a pointed tip defined at the distal or free end portion thereof, and wherein the pointed tip includes the one or more bevels formed thereon. In example forms, the bevels are generally inclined obliquely inward towards the central axis of the staple, whereby the inward directed bevels are configured to guide the legs such that they diverge from the central axis as the bone staple is inserted in the bone. In this manner, the diverging of the legs causes the bone segments engaged by the bone staple to compress against the legs and consequently against each other, creating a comprehensive and symmetric or poly-axial compressive effect as the staple is driven into the bone.

Optionally, a bone screw is provided for extending through the central opening of the crown portion and inserting in the bone. According to one form, the bone screw is generally aligned or coaxially oriented relative to the bone staple when extending through the central opening and engaged within the bone such that the bone screw is generally co-axial with the central axis. According to another form, the bone screw is oriented obliquely relative to the bone staple when extending through the central opening and engaged within the bone such that the bone screw is generally oriented at an oblique angle relative to the central axis of the staple. In example forms, the central opening of the crown portion comprises a chamfered edge defined between the central opening and the top surface of the crown portion such that a portion of the bone screw can be generally recessed or countersunk therein and/or for providing a seating area when the bone screw is oriented at an oblique angle. Optionally, one or more articulation wires can be provided for passing through one or more of the peripheral openings and around one or more of the legs such that the legs may be selectively bent or having a force applied thereto upon tensioning of the articulation wire(s) to impart a selective axial or poly-axial compressive effect to the bone.

In another aspect, the invention relates to bone fixation device including a crown portion and an engagement portion, and an outer rim generally defined between the crown portion and the engagement portion. The engagement portion includes a plurality of legs extending from the outer rim away from the crown portion. The plurality of legs are generally radially disposed and evenly spaced apart around the outer rim. Each of the plurality of legs includes at least one bevel formed thereon to provide for symmetric and directional movement or flexure of the plurality of legs in an outward direction when being inserted within a bone.

In example forms, the crown portion is generally circular in shape and defines a diameter, the diameter generally being between about 8 millimeters to about 26 millimeters. According to particular example forms, the diameter of the crown portion is generally between about 12 millimeters to about 20 millimeters. In example forms, at least one of the plurality of legs has a first length and wherein at least another one of the plurality of legs has a different second length. According to one example form, the first and second lengths of the legs comprise a ratio L1:L2 of about 2:1. According to one preferred form, the engagement portion includes about ten legs extending therefrom wherein about five of the legs have a first length and wherein about five of the legs have a second length, and wherein the legs alternate in length between the first length and the second length around the outer rim. Generally, each of the legs include an outer surface, an inner surface, side surfaces, and a pointed end defined at the end portion thereof, and wherein the pointed end has the at least one bevel formed thereon. According to a particular example form, the crown portion includes a central opening and at least one adjacent or peripheral opening generally positioned near the central opening, and a central axis generally axially extending through the central opening and parallel to the legs. The bevels are generally directed inward towards the central axis, and whereby the inward directed bevels are configured to guide the legs such that they flex and outwardly and diverge from the central axis as the bone staple is inserted in the bone. In this manner, he diverging outward flexure of the legs causes the bone segments engaged by the bone staple to compress against the legs and consequently against each other such that legs and the bevels generate a comprehensive and symmetric compressive effect as the staple is driven into the bone.

In still another aspect, the invention relates to method of holding two or more bone segments in approximation and applying compression to the bone segments. The method includes providing two bone segments in approximation; providing a bone staple having a crown portion and an engagement portion, the engagement portion having a plurality of legs extending therefrom, the plurality of legs including bevels formed at the ends thereof; placing the bone staple against the bone segments in approximation whereby the bevels of the legs are generally adjacent the bone of the bone segments; and driving the legs within the bone of the bone segments, the legs generally symmetrically diverging outwardly such that the bone of the bone segments is compressed and thereby securing the bone segments together in approximation.

In yet another aspect, the invention relates to a method of performing an orthopedic surgical procedure to join two bone segments in approximation with one another. The method includes preparing a bone for fusion or repair; stabilizing the bones with a pin, a clamp, a screw or by one or more hands; providing a sizer; bringing the sizer against the bones to be fixed and centering the sizer relative thereto; determining the appropriate size of a bone staple to be used to secure the bones together based on the size of the sizer relative to the size of the bones; providing a drill template; placing the drill template in the appropriate position relative to the bones and forming pilot holes; providing a bone staple comprising a crown portion and an engagement portion, the engagement portion comprising a radial array of legs of alternating length; and impacting the staple to cause engagement of the staple with the bones, thereby inserting the legs into the bones. Optionally, one or more specific openings formed on the crown portion and corresponding legs on the engagement portion are identified, and a wire loop is placed around the legs and through one or more of the openings. In one form, the wire is tensioned as desired to articulate or apply force to the leg(s) to create compression. Further optionally, a central screw is provided and placed within a central opening of the crown portion and tightened within the bone. Alternatively, the bone screw is placed within the central opening and tightened within the bone and then an articulation wire is tensioned as desired to create compression. Further optionally, prior to insertion of the bone staple into the bones, an articulation wire can be tensioned to apply force or bending of one or more of the legs and then the bone staple with one or more of the legs being bent from the tensioned wire can be inserted into the bones. Optionally a bone screw can then be placed within the central opening of the crown portion and engaged with one or both of the bones.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments the invention are exemplary and explanatory of the invention, and are not restrictive of the invention, as claimed.

BRIEF DESCRIPTION OF THE DRAWINGS

FIG. 8 is a front perspective view of the bone fixation device of FIG. 6 showing a portion of the legs of the bone fixation device and the bone screw fastener partially inserted within a bone.

FIG. 9 is a front perspective view of the bone fixation device of FIG. 8 showing the legs of the bone fixation device and the bone screw fastener fully inserted within the bone.

FIG. 10 is a front perspective view of the bone fixation device of FIG. 7 showing the legs fully inserted within the bone and showing the bone screw fastener inserted within the bone and oriented in an oblique manner.

DETAILED DESCRIPTION OF EXAMPLE EMBODIMENTS

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1A:
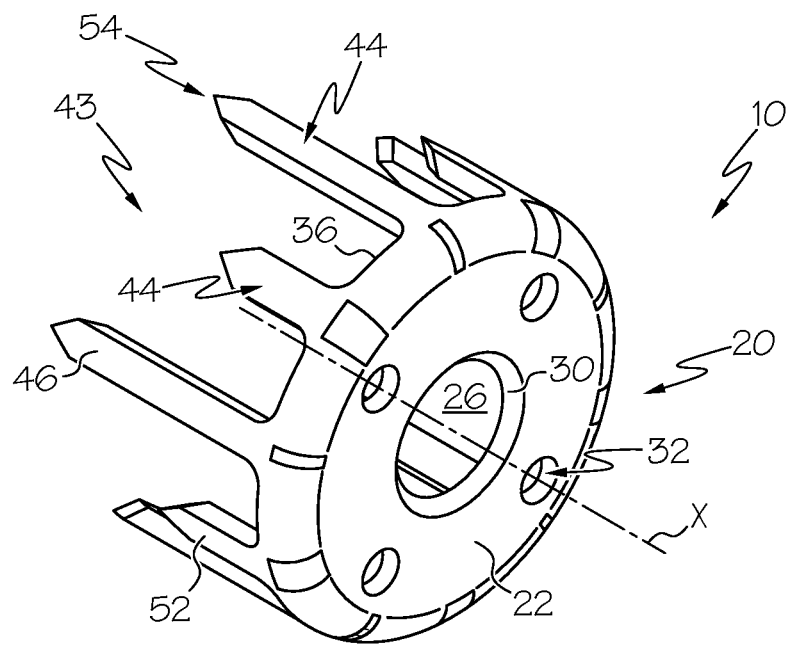
FIG. 1A is a front perspective view of a bone fixation device according to an example embodiment of the present invention.
Figure 1B:
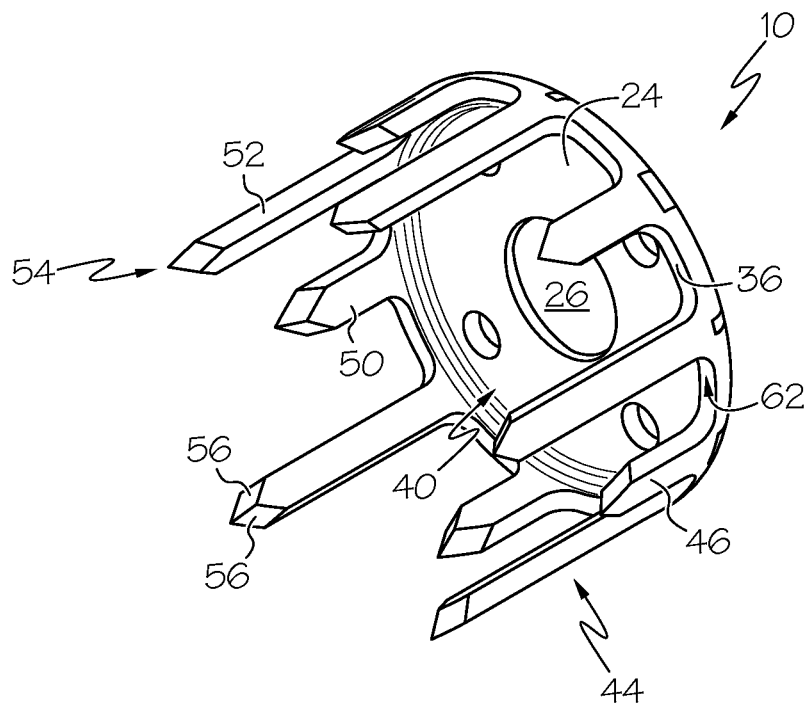
FIG. 1B is a rear perspective view of the bone fixation device of FIG. 1A.
Figure 2A:
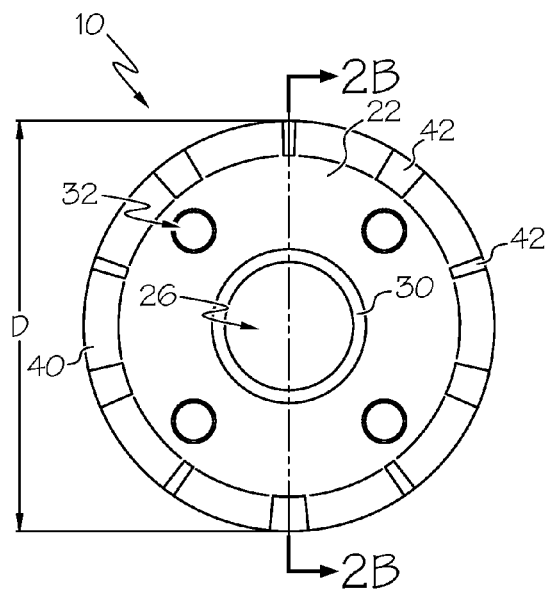
FIG. 2A is a top view of the bone fixation device of FIG. 1A.
Figure 2B:
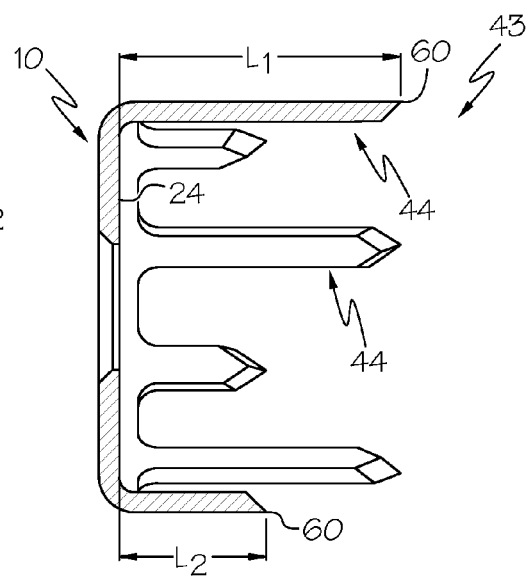
FIG. 2B is a cross-sectional view of the bone fixation device of FIG. 2A taken along line 2B-2B.

With reference now to the drawing figures, wherein like reference numbers represent corresponding parts throughout the several views, FIGS. 1-2 show a bone fixation device, orthopedic implant or bone staple 10 according to an example embodiment of the present invention. As depicted, the bone staple 10 is generally provided for securing bone ends or segments 120 in approximation (e.g., securing two bones 116 together), for example, whereby the bone staple 10 optionally provides for creating a comprehensive symmetric or selectively applied axial or poly-axial compressive effect as the staple 10 is installed in the bone segments.

The bone staple 10 generally comprises a crown portion 20 and an engagement portion 43. According to example embodiments, the bone staple 10 is generally formed from a material suitable for internal medical applications in human or animal patients, for example, a metal such as stainless steel, titanium, aluminum, plastics, or other natural or synthetic materials. Optionally, as will be described below, other materials such as shape-memory materials may be provided for facilitating deformation or transformation of the shape of one or more portions of the bone staple 10 when an external energy source (e.g., heat, electricity, etc.) is applied to the bone staple 10.

In example forms, the crown portion 20 is generally circular in shape; however, other shapes may be employed, for example, oval, polygonal, square or rectangular, etc. In example forms, the bone staple 10 may be sized as desired, for example, wherein the size of the bone ends to be secured together determines the size of the staple to be used. According to one form, the bone staple can be sized such that the diameter D of the crown portion 20 is generally between about 8 millimeters to about 26 millimeters, more preferably between about 12 millimeters to about 20 millimeters (see FIG. 2A). Optionally, the diameter D may be sized as desired.

The crown portion generally comprises a circular body comprising top surface 22, a bottom surface 24, a central opening 26 and one or more adjacent peripheral or circumferential openings 32. The central opening 26 may be provided for connecting the bone staple 10 to a tool, for example, for insertion of the bone staple 10 into the bone ends (see FIGS. 28A-B). According to some example forms, the central opening 26 is configured for receiving a fastener such as a bone screw 64 (see FIG. 3), for example, to further fasten or secure the bone staple 10 to the bone ends 120. Similarly, the one or more adjacent peripheral openings 32 may be provided for receiving one or more additional fasteners such as a wire 74 for affixing bone or articulation of the staple legs, sutures, or other fasteners (see FIG. 5). Alternatively, any of the openings 26, 32 may serve as an entry point for temporary stabilizers upon which the implant can rest prior to final insertion into the bone.

In example embodiments, the central opening 26 generally comprises a chamfered or beveled edge 30 that is formed between the top surface 22 and the opening 26, which preferably facilitates in allowing the bone screw 64 to become recessed or countersunk within the opening and/or for orienting the bone screw 64 at an oblique angle relative to a central axis X extending generally axial through the central opening 26. Similarly, the one or more of the adjacent peripheral openings 32 can optionally comprise a chamfered edge as desired. According to example forms, the outer perimeter of the crown portion 20 defines an outer rim 36 that is generally radiused and defines radiused portions 40 along its outer and inner portions. Generally, the radiused portions 40 are substantially constant around the perimeter of the crown portion 20. According to some example forms, one or more raised surface features 42 are provided around the perimeter of the crown portion 20 and are generally in close proximity with the outer radiused portion 30.

The engagement portion 43 extends from the outer rim 36 in a direction generally transverse to the crown portion 20. In example forms, the engagement portion 43 comprises a plurality of legs 44 extending from the crown 20. In example embodiments, the legs 44 optionally have two or more different lengths, alternating about the circumference of the crown 20. The legs 44 preferably have sharply pointed tips at their distal or free ends 54. According to one example form, the engagement portion 43 comprises ten legs 44, whereby five of the legs 44 are generally sized to define a first length L1 and the other five legs 44 are sized to define a different second length L2. The length is generally defined between the bottom surface 24 of the crown portion 20 and a point 60 defined at the end of the leg 44 (see FIG. 2B). Alternatively, the engagement portion 43 may comprise more or less than ten legs 44 as desired. According to one form, the first length L1 is generally between about 5 millimeters to about 15 millimeters, more preferably between about 7.5 millimeters to about 12.5 millimeters, and the second length L2 is generally between about 1.5 millimeters to about 8.5 millimeters, more preferably between about 3.75 millimeters to about 6.25 millimeters. According to some example forms, the first and second lengths L1, L2 of the legs 44 comprise a ratio L1:L2 of about 4:1, more preferably about 3:1, and more preferably about 2:1. Alternatively, the second length L2 is generally about 0.125% the length of the first length L1, more preferably the second length L2 is generally about 0.25% the length of the first length L1, and more preferably the second length L2 is generally about 0.50% the length of the first length L1. In alternate embodiments, the first and second lengths L1, L2 can be sized and proportioned otherwise, as desired.

In example forms, the legs 44 are positioned to extend from the outer rim 36 and are generally evenly spaced apart circumferentially around the entirety of the outer rim 36 to define a radial array of legs 44. As described above, the legs 44 generally alternate between lengths around the perimeter, for example, wherein each leg 44 of the first length L1 is generally positioned between legs 44 of the second length L2. Similarly, each leg 44 of the second length L2 is generally positioned between legs 44 of the first length L1. As will be described in greater detail below, legs 44 of alternating length preferably provide for greater securement to the bone and prevent a "biscuit-cutter" detachment effect.

Figure 3:
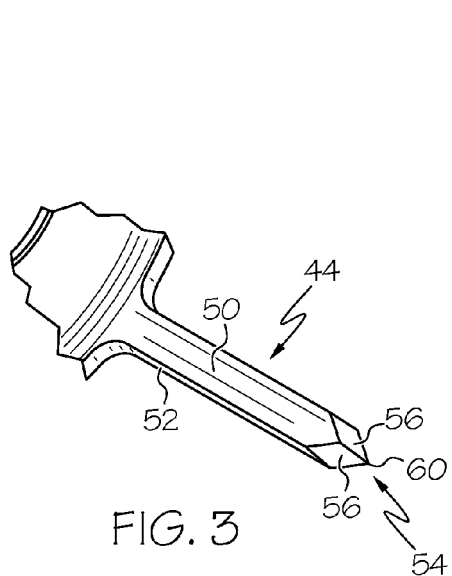
FIG. 3 is a bottom perspective view of a portion of the bone fixation device of FIG. 1A showing portions of a leg extending therefrom.

As shown in FIGS. 1-3, each leg 44 generally comprises an outer surface 46, an inner surface 50, side surfaces 52 and a pointed end 54. Preferably, the outer and inner surfaces 46, 50 are generally radiused to follow the curvature of the outer and inner periphery of the outer rim 36, and the side surfaces 52 generally comprise tapered or beveled edges such that they follow a radius circumferentially in line with the leg and are directed towards the central axis X. The pointed end 54 generally comprises one or more obliquely inclined bevels 56 defining a point 60. In the depicted embodiment, each tip 54 comprises a pair of angularly offset faceted bevels 56 along its internal face. Preferably, the bevels 56 are directed inward towards the central axis X and are configured to guide the legs such that they diverge from the central axis X as the staple is inserted into the bone. This diverging of the legs 44 causes the bone captured beneath the bone staple 10 to compress against the staple legs 44 and consequently each other. Thus, according to example forms, the bevels 56 and legs 44 thereof provide for creating a comprehensive, symmetric compressive effect as the staple is driven in the bone 116. In another way, the bevels 56 effect a directional force on the leg as it enters into a hard substrate such as bone 116. In example forms, the legs 44 will diverge from the axis X upon insertion, and due to the physical properties thereof, the substance (e.g., bone) will be pushed inward against the legs 44 pushing outwards, thereby creating a compressive effect internally and beneath the bone staple 10. Furthermore, the bevels 56 preferably provide additional benefits such as preventing rotation of the staple when inserting the same into bone, and wherein the surface area in contact with bone is increased, thereby further enhancing resistance to pulling out due to distractive forces. In alternate embodiments, selected legs 44 are provided with inwardly tapered beveled tips as described, and other legs 44 are provided without inwardly tapered beveled tips, causing only selected legs to apply compressive force upon installation, allowing for selective application of compression in one or more axes as desired by an orthopedic practitioner.

According to example forms, each of the legs 44 are connected to the outer rim 36 whereby a transitional radiused portion 62 (see FIG. 1B) is provided between the side surfaces 52 and the exposed surface of the outer rim 36, for example, to substantially increase the rigidity of the leg and reduce the likelihood of the leg 44 bending in a side-to-side or radial direction relative to the central axis X. However, the legs 44 are preferably configured such that they are capable of resilient flexure, bending towards and away (e.g., inwardly and outwardly) relative to the central axis X, for example, to accommodate the intended functionality of diverging away from the central axis X to provide for polyaxial compression of the bone ends 120. In example forms, the legs 44 are substantially rigid along the length thereof, but at least partially flexible and resilient along their lengths and/or near their points of attachment to the outer rim 36. Thus, according to example forms, the legs are capable of elastic deformation whereby the bending thereof in the inward and outward directions does not cause a concern for stress risers, cracking, or other plastic deformation likely to cause failure of the legs 44, and thus, permanent separation of the legs 44 from the outer rim 36.

As shown in greater detail in FIG. 3, the bevels 56 are generally symmetrically formed about the end of each leg 44 whereby the point 60 is generally positioned at the midpoint of the leg 44 and whereby an edge is defined between the two bevels 56. According to example forms, the surfaces of the bevels 56 are generally configured such that the top edge portions of the bevels 56 are generally adjacent the inner surface 50 of the leg 44, and whereby the surface is directed downwardly and outwardly until intersecting with the outer surface 46 of the leg 44. Optionally, as described above, the angular orientation of the surfaces of the bevels 56 causes the legs 44 to diverge outwardly as they are being inserted within the bone such that compression of the bone ends can be achieved (as will be described below).

Figure 4:
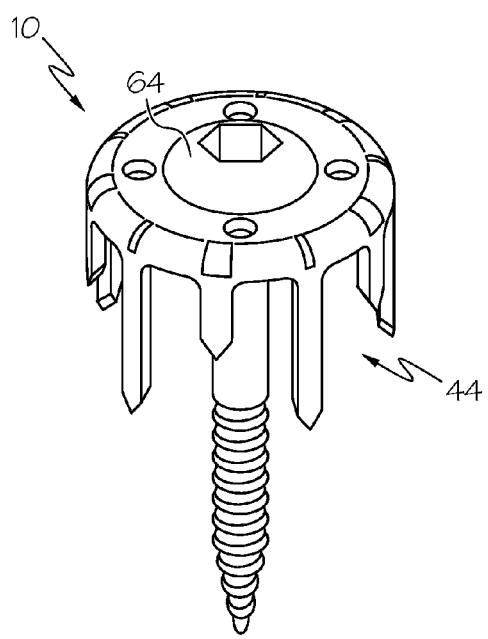
FIG. 4 is a top perspective view of the bone fixation device of FIG. 1A showing a bone screw fastener extending through a portion thereof.
Figure 5:
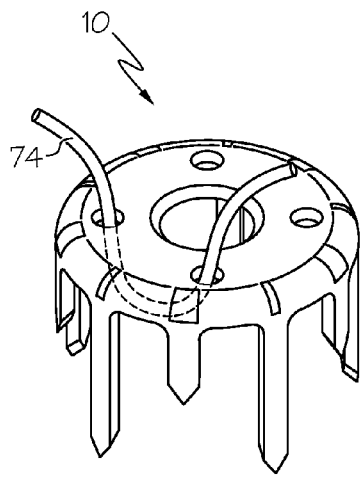
FIG. 5 is a top perspective view of the bone fixation device of FIG. 1A showing a wire fastener extending through a portion thereof.
Figure 6:
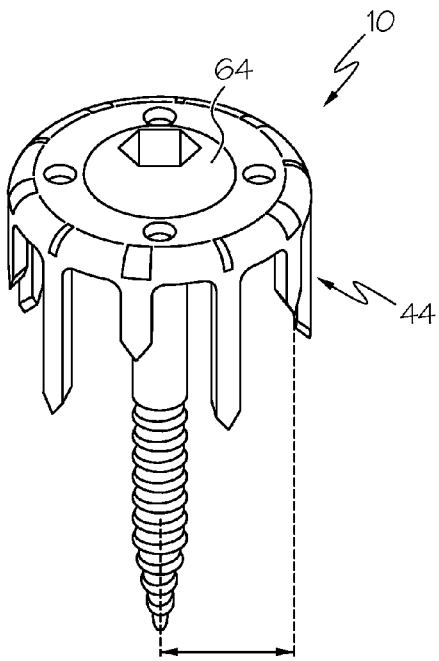
FIG. 6 is a front perspective view of the bone fixation device of FIG. 3.
Figure 7:
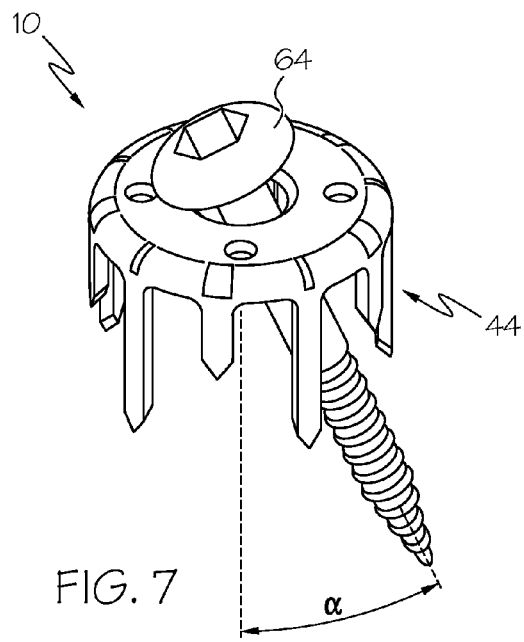
FIG. 7 is a front perspective view of the bone fixation device of FIG. 6 showing the bone screw fastener extending through a portion thereof in an oblique manner.

FIGS. 4-5 show the bone staple 10 comprising additional fasteners, for example, such as a bone screw 64 or wire 74. As shown in FIGS. 4 and 6, the bone screw 64 is generally co-axial with the legs 44, however, according to some example forms, the bone screw 64 can be oriented at an oblique angle $\alpha$ relative to the axis X (see FIG. 7). As described above, the chamfered edge 30 preferably permits the bone screw 64 to be oriented at an oblique angle $\alpha$ up to a limit where collision with a leg 44 would occur.

FIGS. 8-9 show the effect of using a bone screw 64 through the central opening 26 to exert a compressive force axially enhancing stability of the bone staple 10. As shown, the central aperture is generally smooth and chamfered whereby the bone screw 64 is generally free to move relative to the bone staple 10. However, the central opening 26 can be provided with threads or other interengagement features to accept coupling or interengagement with an insertion tool or screw head as desired. As depicted in FIG. 10, the bone screw 64 oriented at an oblique angle $\alpha$ with the bone staple 10 inserted into the bone 116, whereby compression is achieved and the bone screw 64 further resists inadvertent pulling out of the bone staple 10 due to axial forces, for example, as illustrated by tool 76 applying an upward force to the crown portion 20.

Figure 11:
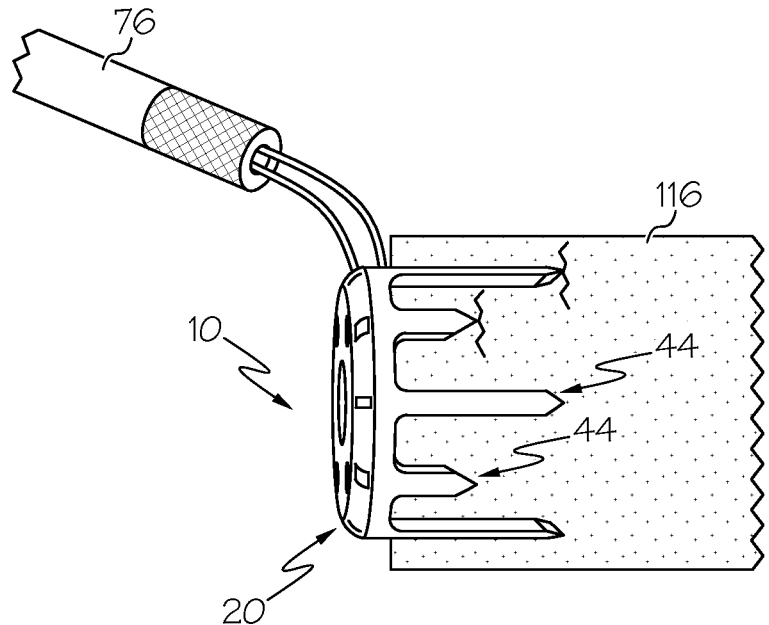
FIG. 11 is a side view of the bone fixation device of FIG. 1A fully inserted within a bone and showing a picking tool engaged with a portion thereof, and whereby the varied lengths of the legs of the bone fixation device provide for securing the bone staple to multiple levels of the bone.
Figure 12:
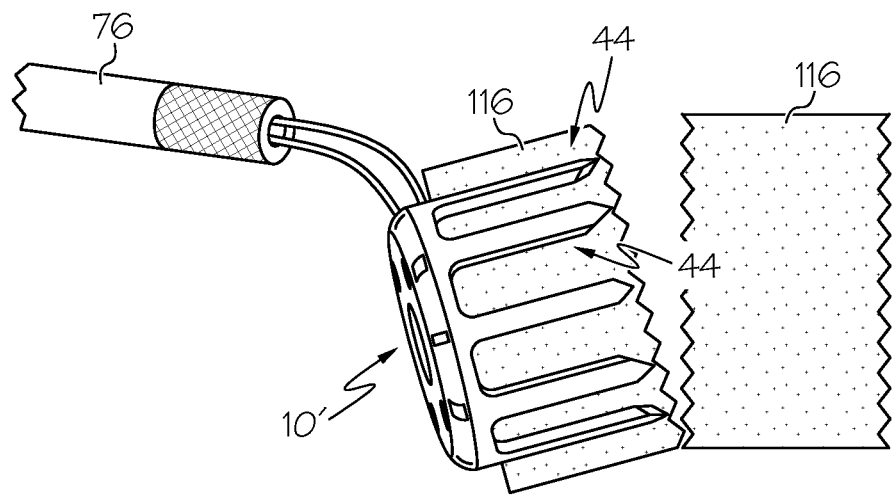
FIG. 12 is a side view of another bone fixation device having a plurality of legs all with the same length, demonstrating a potential "biscuit-cutting" detachment mode, which is resolved or improved upon by provision of legs of differing lengths.

FIGS. 11-12 show the advantage of variation the length of the legs 44 around the perimeter of the crown portion 20 that are engaged with the bone 116. As shown in FIG. 11, the length of the legs 44 alternate between the first length L1 and the second length L2, which preferably provides for multiple levels of bone to be secured by the staple and more robust fixation. By contrast, FIG. 12 shows a bone staple 10' where the length of all legs 44 is the same or substantially similar, in which case generally the same levels of bone are secured by each leg of the staple. In some cases, this configuration can cause a "biscuit-cutter" detachment or failure, wherein the bone engaged by the staple detaches from surrounding bone near the ends of the legs. In some applications, however, a bone staple with legs of similar lengths may be utilized without such results.

Figure 13:
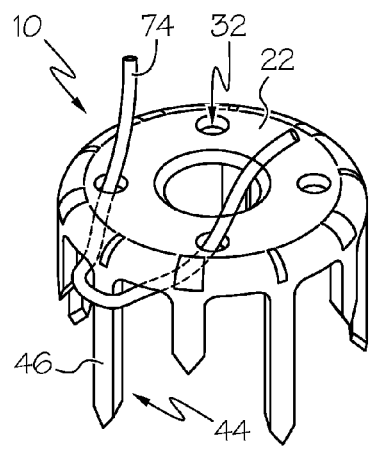
FIGS. 13-15 show the bone fixation device of FIG. 1A whereby one or more articulation wires are positioned through peripheral openings and around legs of the bone fixation device to provide selective compression of the bone.
Figure 14:
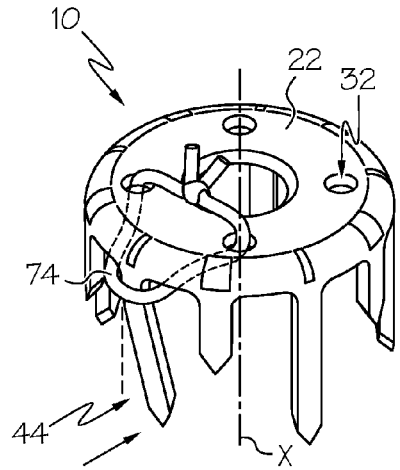
Figure 15:
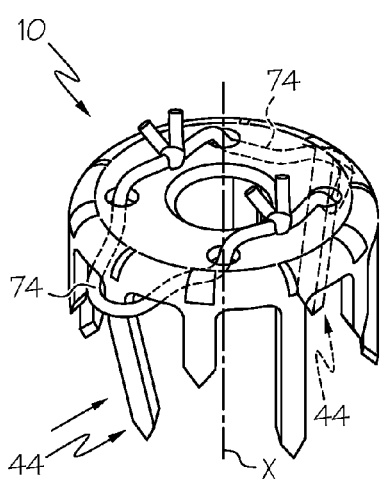

FIGS. 13-15 show systems and methods according to example forms of the invention, wherein one or more articulation wires 74 are applied to apply force or flexure upon one or more of the legs 44 towards the central axis X. As depicted in FIG. 13, an articulation wire 74 is preferably inserted through one of the adjacent peripheral openings 32, passing around and across the outer surface 46 of one or more of the legs 44, and then inserted back through another one of the adjacent peripheral openings 32 such that both ends of the wire are accessible and adjacent the top surface 22 of the crown portion 20. In example forms, the articulation wire 74 is preferably looped through the bone staple 10 prior to the bone staple 10 being inserted into the bone, and then once the bone staple 10 is inserted into the bone, the articulation wire 74 is tensioned, for example by twisting the wire upon itself, to apply inwardly directed force and/or bending of the engaged legs 44 such that an effect of selective compression of the bone ends is accomplished. Alternatively, according to other example forms, the articulation wire 74 is tensioned to cause the one or more legs to bend prior to insertion into the bone. Generally, when utilizing the articulation wire 74 as a fastener, the leg 44 to be captured by the wire 74 is generally the longer of the two lengths (e.g., the first length L1). However, in some example forms, the leg 44 can be the shorter of the two lengths, or a combination of the two. FIG. 13 shows the articulation wire 74 capturing a single leg 44 wherein the ends are extending through a pair of the adjacent openings and generally positioned adjacent the top surface 22 of the crown portion 20. FIG. 14 shows the wire 74 tensioned whereby the leg 44 is generally bent inwardly towards the central axis X whereby the ends of the articulation wire 74 are tied in a knot or otherwise twisted or connected together to provide a firm engagement therebetween. FIG. 15 shows a bone staple comprising two articulation wires 74 whereby two legs 44 are captured by the articulation wires 74 and being bent inwardly towards the central axis X and further enhancing compression of the legs towards each other and thus the underlying bone ends. In alternate embodiments, a "tension band" can be created using the multiple apertures available to the user (e.g., central and adjacent openings), to further enhance compression of one or more legs towards each other and thus the underlying bone ends. Optionally, one longer wire may be provided for looping through the adjacent openings to capture two or more of the legs 44 as desired, for example, such that only one knot is required for tensioning the wire and causing compression of the two or more legs 44. By selective application and controlled tensioning of one or more articulation wire(s) 74 about one or more selectively positioned leg(s) 44, an orthopedic practitioner may apply compression to engaged bone tissue in one (axial) or multiple different (poly-axial) directions or axes, as deemed clinically appropriate for a particular application or procedure.

Figure 16:
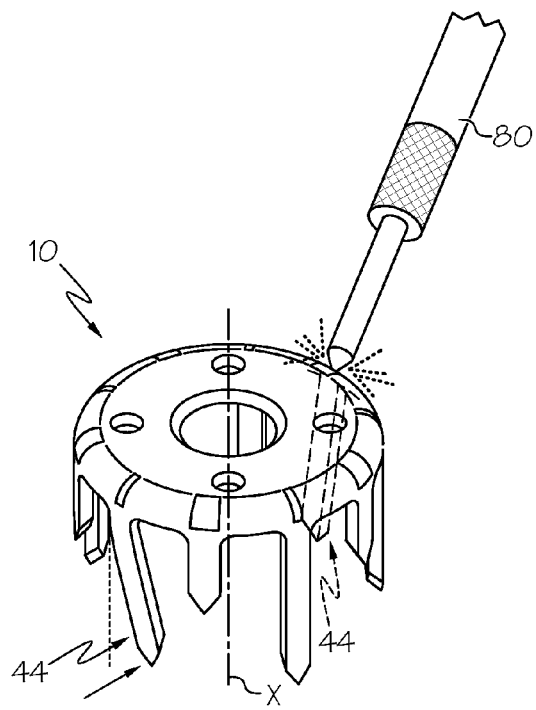
FIG. 16 shows a front perspective view of the bone fixation device of FIG. 1A whereby external energy is applied thereto to effect bending of one or more legs for selective application of compression.

FIG. 16 shows an external energy device or probe 80 being employed to cause multiple legs 44 of the bone staple to compress towards the central axis X. According to example forms, the external energy device 80 may take the form of heat or electricity, and the bone staple, or at least the legs thereof, may be formed from a material conducive to shape memory whereby one or more forms of energy being applied thereto causes a transformation in shape. Thus, according to example forms of the present invention, a compressive effect can be generated through the mechanism afforded by shape-memory metals such as Nitinol (shape memory effect nickel-titanium alloy). In another way, the application of heat energy to the staple after implantation into a bone will effect a movement of the staple legs. When manufactured, the shape-memory position represents the near complete apposition of the staple legs. The device is pre-bent to a neutral leg position for implantation (e.g., the legs generally extending substantially perpendicular relative to the crown portion), and the application of a heat source causes the legs to return to the compressive state whereby they compress inwardly towards the central axis X. Using the same geometry as a staple made from titanium, stainless steel, or plastics, the shape-memory alloy (e.g., Nitinol or other similar materials) can exert the compressive effect without the use of additional wire material.

Figure 17:
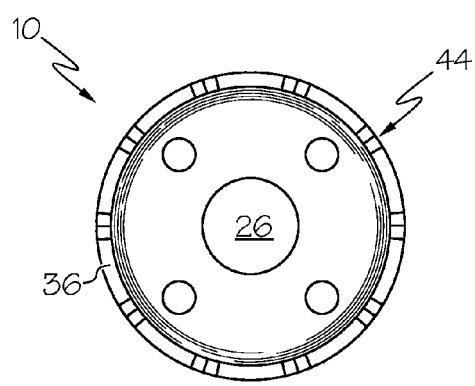
FIG. 17 shows a bottom view of the bone fixation device of FIG. 1A.
Figure 18:
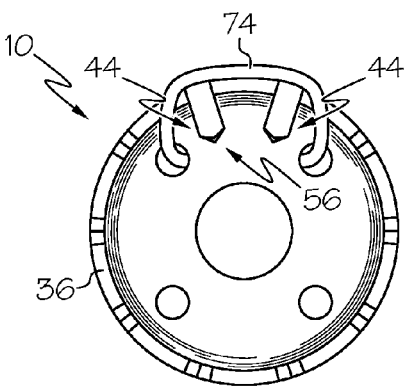
FIG. 18-19 show bottom views of the bone fixation device of FIG. 17 whereby one or more articulation wires extend through peripheral openings of the bone fixation device such that one or more legs of the bone fixation device are bent inward towards a central axis thereof to provide for compression against the bone.
Figure 19:
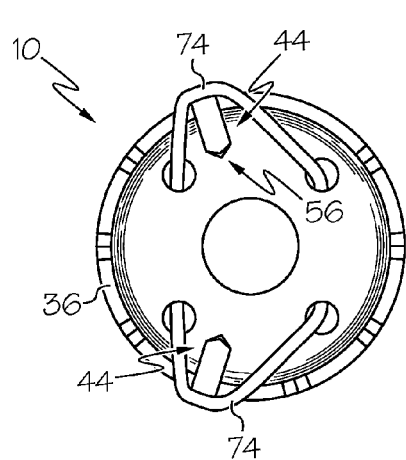

FIGS. 17-19 show bottom views of the bone staple further demonstrating application of articulation wires 74. As depicted, the radially disposed legs 44 follow along the outer rim 36 of the crown portion 20 whereby bone or other substrate can be captured in a plurality of angles. As shown, the angles of the bevels 56 can be seen as radially oriented with respect to the perimeter of the crown portion 20. Preferably, the radial pattern of the legs 44 is configured such that the bevels 56 are directed inwards towards the central axis X. Preferably, by the bevels being configured at such inwardly-directed angles, the legs 44 diverge outwardly away from the central axis X when inserted into the bone. As depicted in FIG. 18, two legs 44 that are adjacent each other are compressed inwardly by a wire 74. As depicted in FIG. 19, two legs 44, which are generally on opposite sides of each other, are compressed inwardly by a pair of wires 74. Optionally, instead of using a pair of wires 74, a single wire may be provide for capturing two or more legs 44, regardless of whether they are adjacent each other or generally positioned across from each other.

Figure 20:
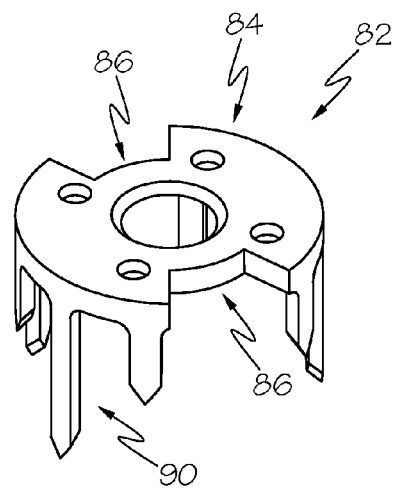
FIG. 20 shows a perspective view of a bone fixation device according to another example embodiment of the present invention.

FIG. 20 shows a bone staple 82 according to another example embodiment of the present invention. As depicted, the bone staple 82 is generally similar to the bone staple 10 as described above. In example forms, the bone staple 82 comprises a crown portion 84 and an engagement portion comprising a plurality of radially-disposed legs 90. As similarly described above, the crown portion comprises a central opening and one or more adjacent openings formed generally near the central opening. According to one example form, the bone staple 82 comprises a pair of cutouts 86 formed within portions of the crown portion 84. The cutouts are generally positioned on opposite sides of the crown portion 84 relative to each other and are generally sized to extend partially within the crown portion 84, however, not to the extent to interfere with the central or adjacent openings. The cutouts 86 generally comprise a generally central radial portion and two substantially linear surfaces extending from the radial portion. Optionally, the cutouts 86 may be shaped and sized as desired.

Figure 21A:
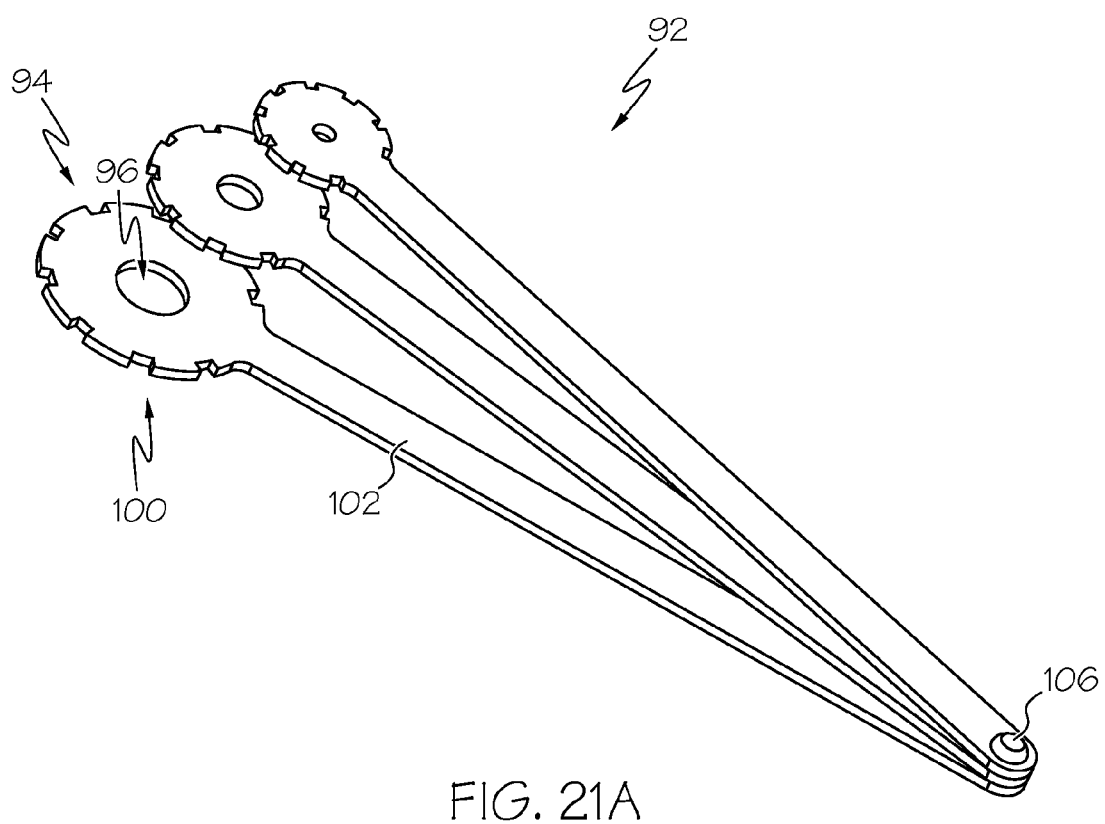
FIG. 21A shows a perspective view of a sizing template assembly according to an example embodiment of the present invention.
Figure 21B:
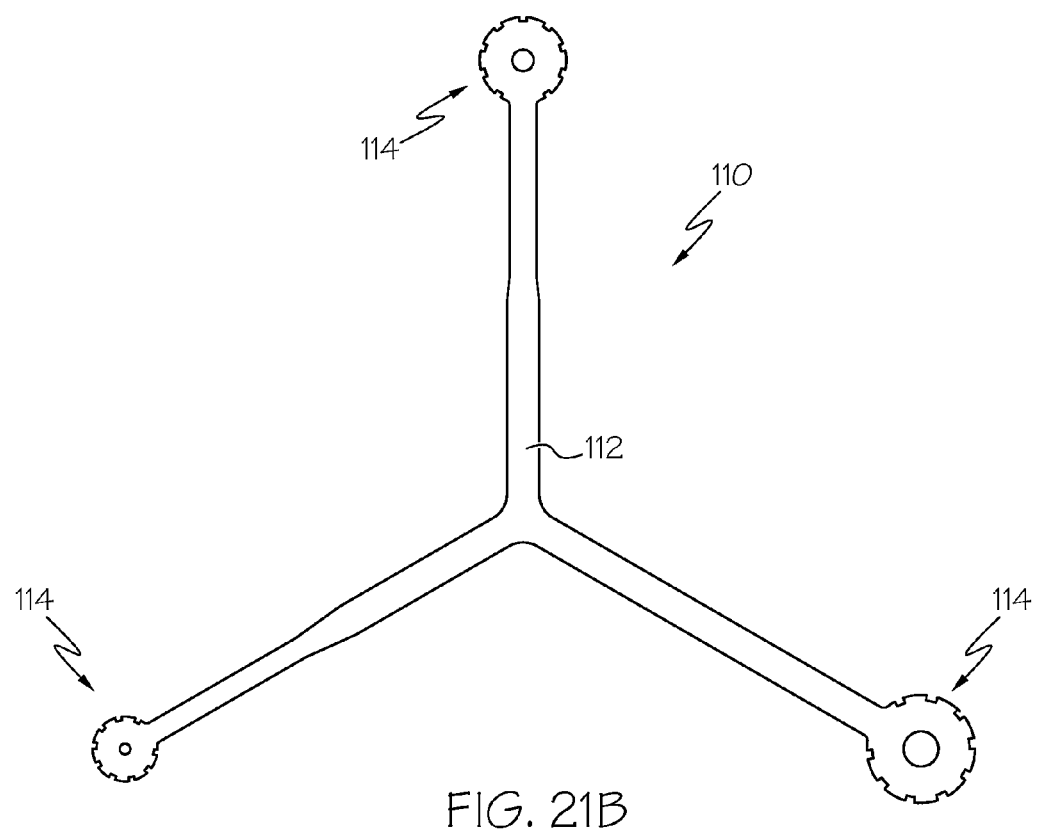
FIG. 21B shows a perspective view of an approximation sizer according to another example embodiment of the present invention.

FIG. 21A shows a sizing template 92 according to an example embodiment of the present invention. In example forms, the sizing template 92 is generally provided for placement on the adjoining bone ends to determine what size staple will be utilized in securing the bone ends together. As depicted, the sizing template 92 comprises a plurality of sizers connected together by a fastener 106, for example, a rivet, screw, or other engagement member. Preferably, the sizers are pivotable about the fastener 106. In example forms, each sizer generally comprises a sizing portion 94 and a handle 102 extending from the sizing portion 94. Generally, the sizing portion 94 comprises a central opening 96 and a plurality of cutouts 100 formed along the perimeter of the sizing portion 94. Generally, the central opening 96 is intended to provide for a visual of the central opening 26 of the bone staple 10 and the plurality of cutouts 100 are intended to provide for a visual of the legs 44 radially disposed around the perimeter of the crown portion 20. In example forms, the clinician or other assistant or surgical professional may place the sizing portion 94 near the adjoining bone ends to determine what size bone staple 10 is appropriate for securing the bone ends 116 together (see FIG. 22). FIG. 21B shows an approximation sizer 110 comprising a Y-shaped body 112 and sizing ends 114. Generally, the approximation sizer 110 is used similarly as the sizing template, however, the sizing ends 114 are fixed relative to each other rather than being movable relative to the fastener 106.

Figure 22:
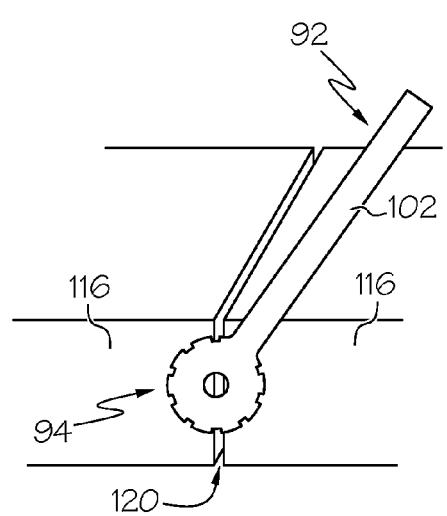
FIG. 22 shows a perspective view of one of the sizing templates of the sizing template assembly being positioned relative to two bone ends positioned in approximation.
Figure 23:
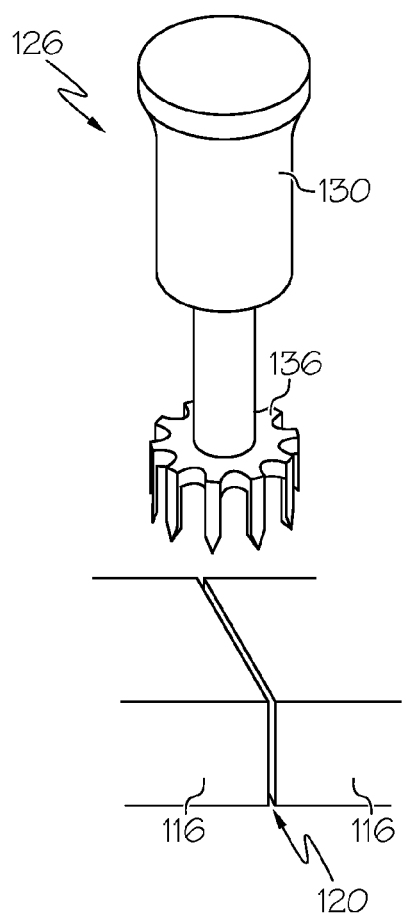
FIGS. 23-26 show a sequence of operation of a punch assembly being used to provide pilot openings within the bone ends in approximation and whereby the pilot openings receive the legs of a bone fixation device according to an example embodiment of the present invention.
Figure 24:
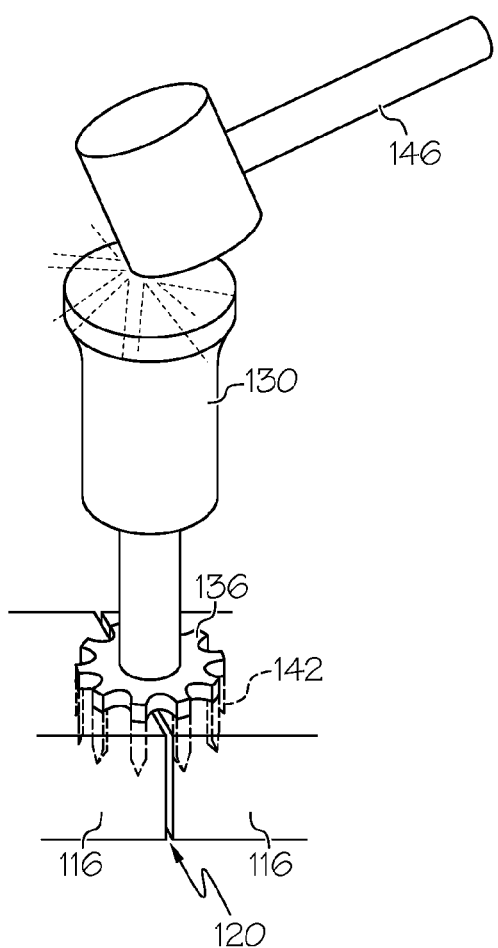
Figure 25:
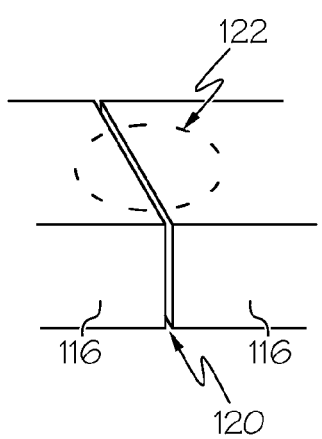
Figure 26:
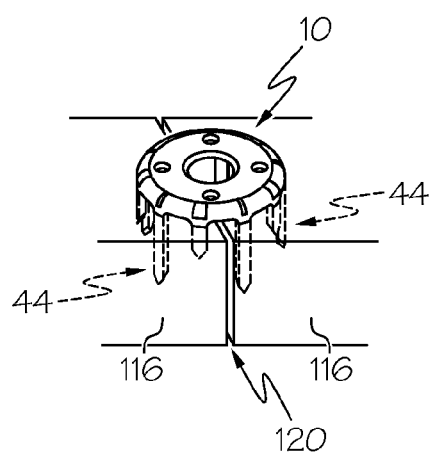

In example procedures and methods of surgical fixation according to the present invention, anatomic dissection is optionally carried out and the bone 120 is surgically exposed. When it is determined that staple fixation is to be employed, the bone ends (if for arthrodesis) or bone segments (if for fracture fixation) are held with a clamp, pin, or manually. A sizing template is optionally held against the surgical site to determine the correct size staple to use, for example, as depicted in FIG. 22. Based on this measurement, a pre-drill tool may be used to establish pilot holes for the implant legs. This may be accomplished by using a smooth trocar pointed wire 184 (see FIG. 32) inserted into the template slots corresponding to staple legs 44, a drill bit 170 (see FIG. 30) inserted into the same template slots, or using a punch tool or assembly 126 having teeth arranged in conformance with the staple configuration that is tapped into the bone 116, and then removed. For example, as depicted in FIGS. 23-25, a punch assembly 126 comprising a punch rod 130 and a punch 136 (comprising teeth arranged substantially similarly as the legs 44 of the bone staple 10) is provided for forming pilot holes in the bone ends 120. As depicted in FIG. 24, a mallet 146 is used to tamp the punch assembly 126 against the bone ends 120, thereby causing the teeth 142 of the punch 136 to be inserted into the bone 116. The punch assembly is then removed to disengage the teeth 142 from the bone 116, thereby leaving a generally circular array pattern 122 of pilot holes, which substantially matches the arrangement of the legs 44 of the bone staple 10 to be installed (see FIG. 25). Once the holes are established, a corresponding bone staple 10 is brought up to the surface of the bones 116 to be stabilized so that the legs 44 are perpendicular to the surface and the pointed ends are engaging the substrate in the holes already made. A bone tamp or punch 196 (see FIG. 33) is then brought up to the crown portion and the mallet 146 is used to tamp the staple into the bone ends 120 (see FIG. 26). Reduction or stabilization clamps or wires are then removed.

In example embodiments, the bone staple may be utilized not only to affix and stabilize bone ends or segments, but optionally also to apply compression to the bone ends or segments. As described above, the staple 10 optionally has bevels 56 at the tips of one or more of its legs 44, which guide the legs 44 to diverge as the staple 10 is inserted. This outward diverging of the legs 44 causes resilient flexure and results in an inwardly directed elastic force within the legs 44, which in turn applies an inward compressive force to the bone 116 engaged between the legs of the staple 10. Therefore, according to some example embodiments, no additional materials or procedures are needed to create a comprehensive, symmetric compressive effect as the staple 10 is driven in. Alternatively, selective axial or poly-axial compression by be applied. When using the compressive effect of a single staple leg 44, the user optionally prepares the device by looping a steel articulation wire 74 around the leg 44 to compress and exiting the wire ends through the peripheral openings 32 in the crown portion 20. After implantation of the staple 10 using the technique described herein, the user then twists the wire ends together, effectively making the knot tighter and applying tension, pulling the staple leg towards the wire apertures. When multiple legs are to be compressed together then multiple peripheral apertures can be used, where the wire would loop around any number of legs to be compressed towards the central axis.

Figure 27A:
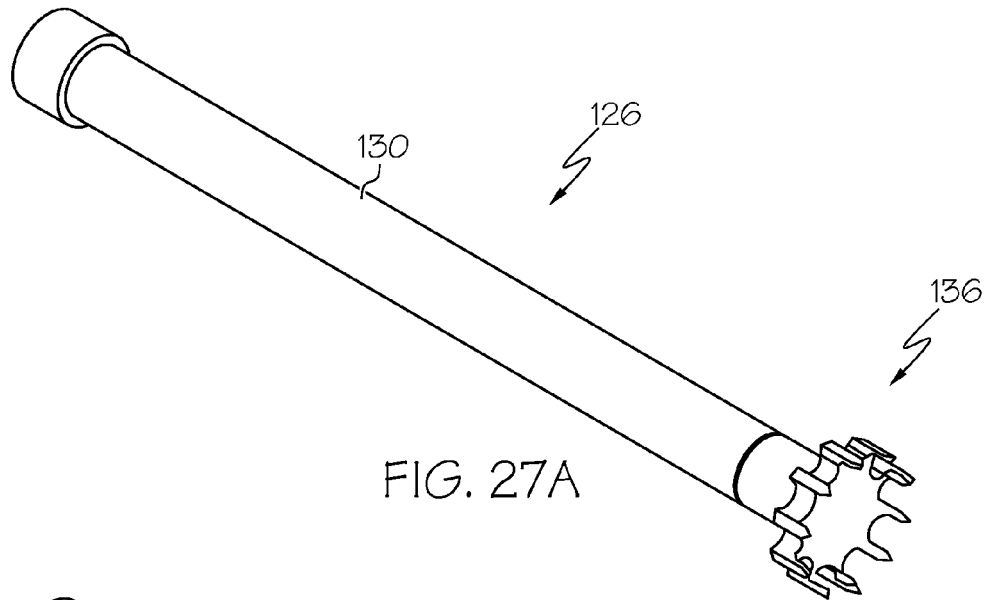
FIG. 27A shows a perspective view of the punch assembly shown in FIGS. 23-24.
Figure 27B:
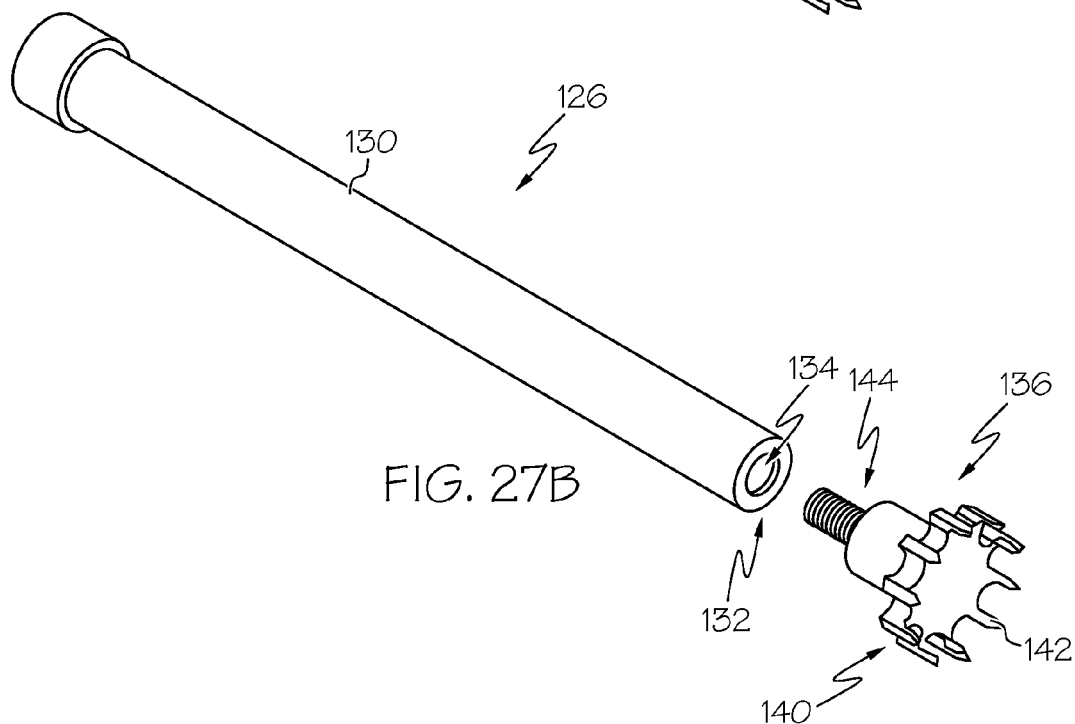
FIG. 27B shows a perspective view of the punch assembly of FIG. 27A, showing the punch disassembled from the punch rod.

FIGS. 27A-B show further details of the punch assembly 126. As described above, the punch assembly 126 comprises the punch rod 130 and the punch head 136. According to example forms, the punch rod 136 comprises a receiving end having a threaded portion 134 and the punch head 136 comprises a crown portion 140 having a radial array of teeth 142 extending therefrom. Furthermore, a threaded rod 144 extends from the crown portion 140 in a direction generally opposite the extension of the teeth 142 for engagement with the threaded portion 134 of the punch rod 130. Preferably, as the bone staple 10 can be sized as desired, the punch 136 preferably can also be sized accordingly such that the radial array of teeth 142 substantially match with the radial array of legs 44 of the bone staple 10, for example, such that the pattern 122 of pilot holes substantially matches with the legs 44 for proper insertion and securement of the bone staple 10 with the bone ends 116.

Figure 28A:
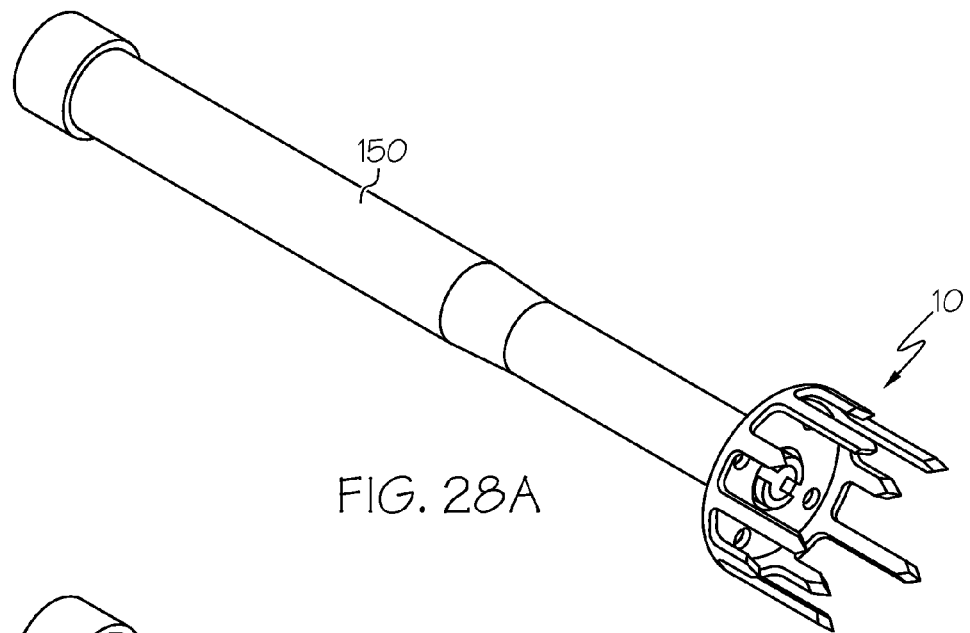
FIG. 28A shows a perspective view of an implantation tool and a preloaded staple assembly according to an example embodiment of the present invention.
Figure 28B:
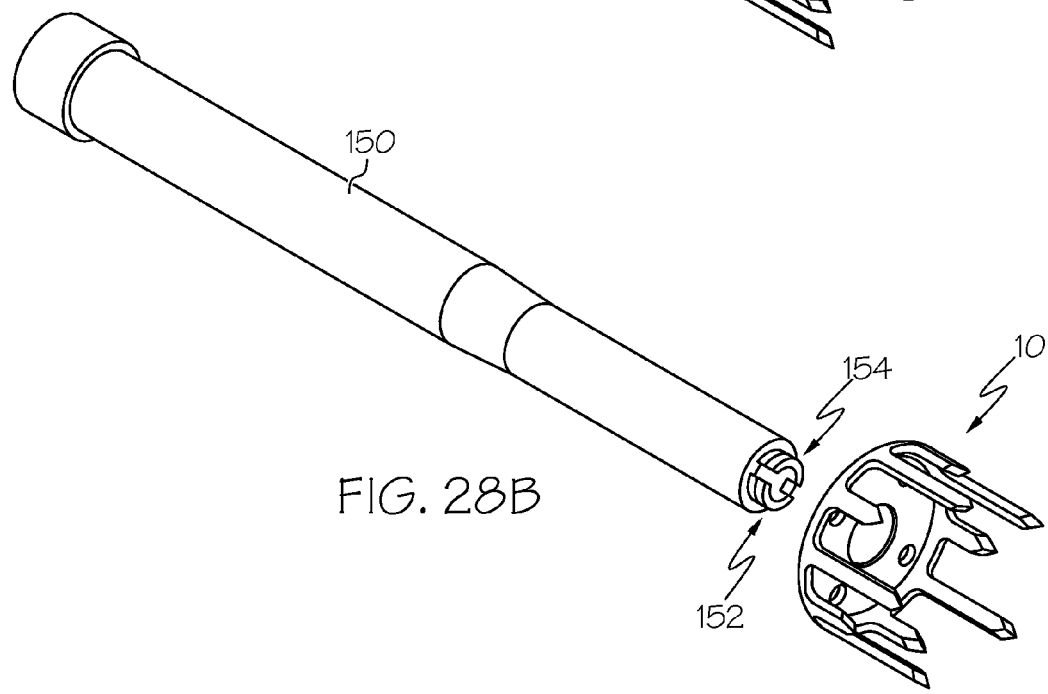
FIG. 28B shows a perspective view of the staple assembly of FIG. 28A, showing the bone fixation device separated from the staple implantation tool.

FIGS. 28A-B show a bone staple assembly rod or implantation tool 150 for providing removable engagement with the bone staple 10 so that the bone staple can be properly secured to the bone ends once the pattern 122 of pilot holes are formed. In example form, the bone staple assembly rod 150 comprises an engagement end 152 comprising a pair of clips 154 that are preferably sized to engage the central opening 26 of the bone staple 10. Preferably, the bone staple assembly rod 150 provide for maneuvering and providing precise and accurate positioning of the bone staple 10 within the pilot holes of the bone ends 120. According to example forms, while the bone staple 10 is still removably coupled to the engagement end 152 of the assembly rod 150, a mallet can be provided for tamping the end of the assembly rod 150 so that the bone staple 10 is fully inserted within the bone 116. Optionally, the assembly rod can be disengaged therefrom once the bone staple 10 is at least partially engaged with the bone 116 so that the punch 196 can be provided for facilitating tamping the bone staple 10 entirely within the bone 116.

Figure 29:
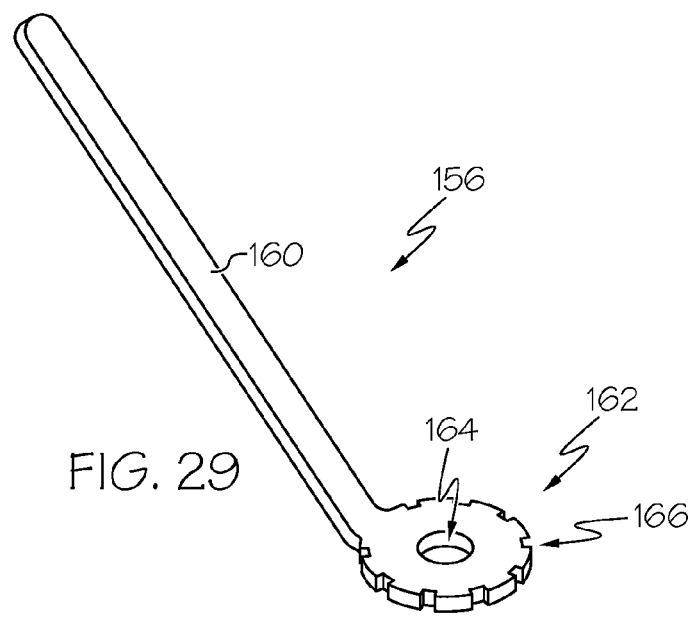
FIG. 29 shows a perspective view of a drill template according to an example embodiment of the present invention.
Figure 30:
FIG. 30 shows a plan view of a drill bit according to an example embodiment of the present invention.
Figure 31:
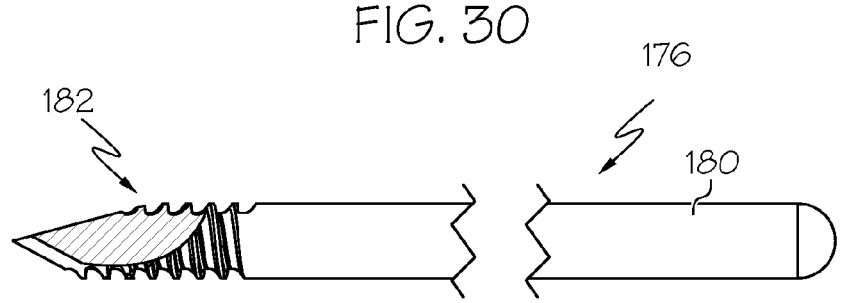
FIG. 31 shows a plan view of a temporary fixation pin according to an example embodiment of the present invention.
Figure 32:
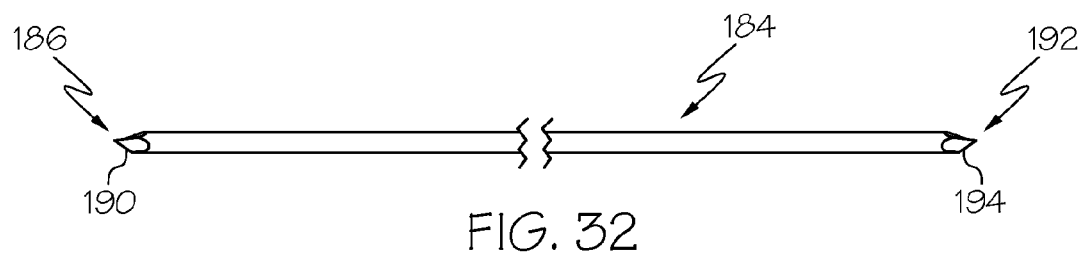
FIG. 32 shows a smooth double trocar wire according to an example embodiment of the present invention.
Figure 33:
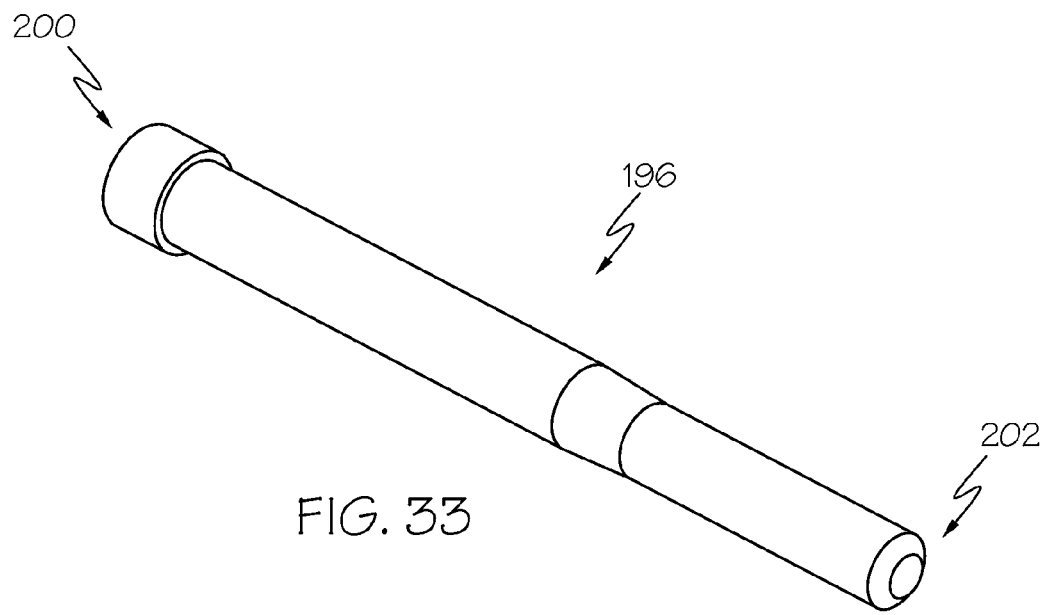
FIG. 33 shows a perspective view of a tamping tool according to an example embodiment of the present invention.

FIGS. 29-33 show additional tools for facilitating the process for securing the bone staple 10 to the bone ends 120. As shown in FIG. 29, a drill template 156 may be provided for providing a template for placement against the bone ends 120 whereby a drill bit 170 can be used to drill a hole within the bone ends 120, for example, wherein a bone screw 64 is desired to provide further securement of the bone staple 10 to the bone ends 120. The drill template 156 generally comprises a handle 160 and an end sizer member 162. The end sizer member 162 preferably comprises a central opening 164 and outer openings 166 substantially matching the radial array of legs 44 of the bone staple. Similarly, the central opening preferably matches the central opening 26 of the bone staple 10. Preferably, the end sizer member 162 may be sized according to the particular size staple to be used, for example, as similarly described with respect to the sizing template 92 and approximation sizer 110. As depicted in FIG. 30, the drill bit 170 generally comprises a cutting portion 172 and a shank portion 174. According to example forms, the diameter or size of the drill bit cutting portion 172 is generally sized to accommodate the bone screw 64. As depicted in FIG. 31, a temporary fixation pin may be provided for temporarily securing the bone staple 10 to the bone ends 120 as desired. The temporary fixation pin 176 generally comprises an elongate rod 180 and a pointed end 182 comprising a bevel and one or more partial threads, for example, to temporarily engage the bone 116. As depicted in FIG. 32, the trocar wire 184 generally comprises a first end 186 comprising a bevel 190 and a second end 192 comprising a bevel 194. According to example forms, the trocar wire 184 can be used to form openings or pilot holes within the bone. As depicted in FIG. 33, the punch 196 comprises a generally elongate member comprising a first end 200 and a second end 202. In example forms, with the second end 202 placed against the crown portion 20 of the bone staple 10, the first end can be tamped by the use of a mallet 146 for inserting and securing the bone staple 10 to the bone ends 120.

Figure 34:
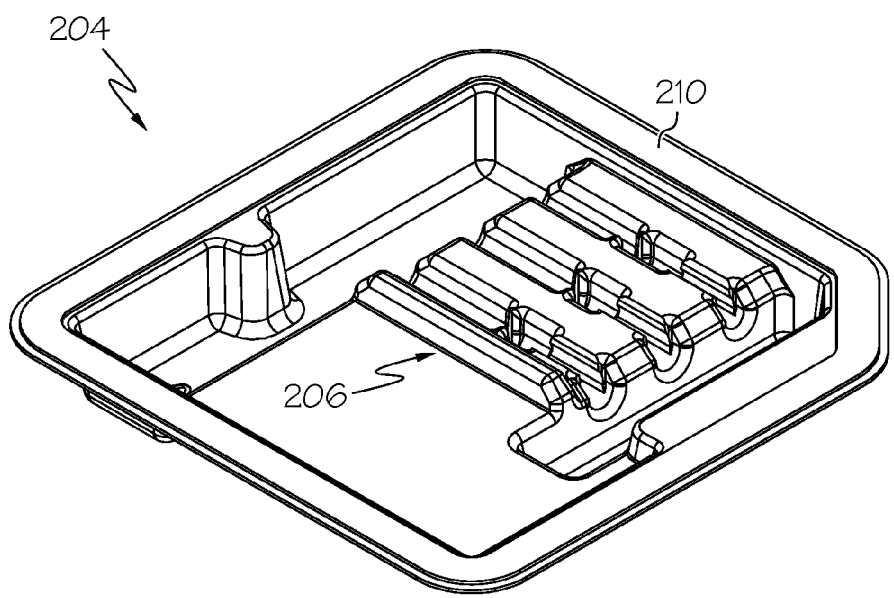
FIGS. 34 and 35 show perspective and plan views of a packaging container for receiving various tools and components including one or more bone fixation devices, and a packaged orthopedic procedure kit according to example embodiments of the present invention.
Figure 35:
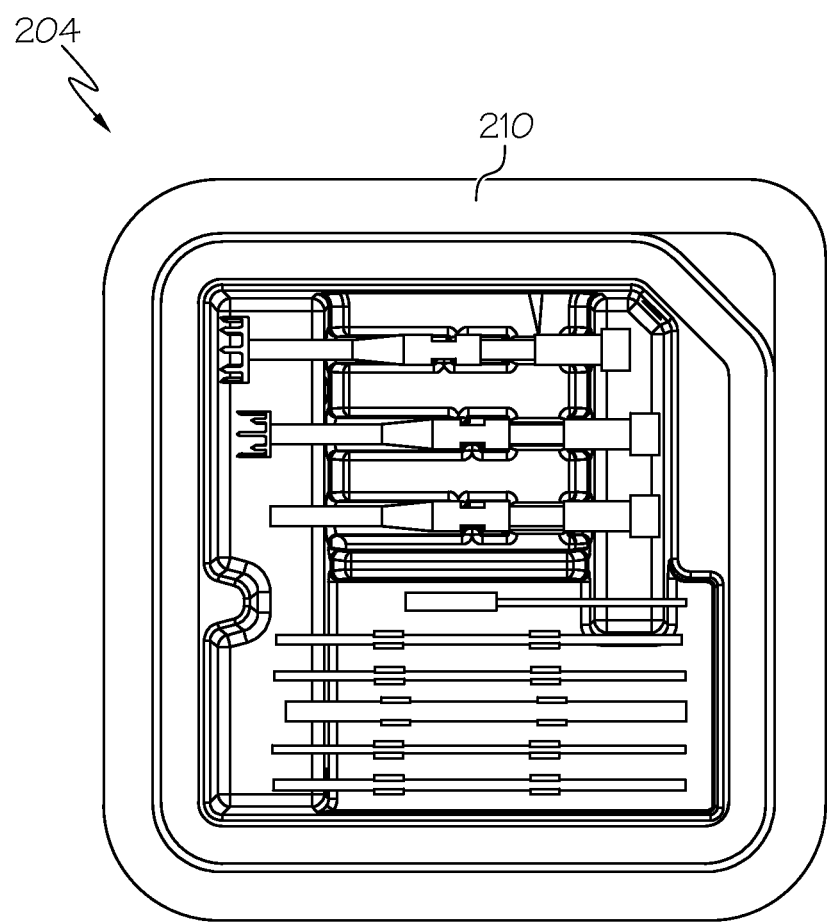

Some or all of the above described preparation and installation tools can be provided together in a packaged kit, along with one or more bone staples, according to further example embodiments of the invention. FIGS. 34-35 show an example packaging tray 204 for use with packaging the bone staples 10 and other tool and elements of the present invention together in a kit, for example, such that an orthopedic practitioner can have all the components and tools for the surgical procedure in one place during the procedure. In example forms, the packaging tray generally comprises one or more receiving portions 206 and a lip 210 generally surrounding the perimeter of the tray such that a film or other protective material can seal thereto to keep the bone staples 10 and other tools, etc. sanitary until the surgical procedure is to be performed. In example forms, a form-fill-seal machine can be utilized to form a plurality of packaging trays 204, whereby a sheet material is generally stamped to form the receiving portions 206 and the lip 210. The kit is assembled in the tray 204 and optionally autoclaved, chemically or otherwise sterilized, and sealed to prevent contamination during storage and transport, until opened for use by the practitioner.

According to further aspects of the invention, surgical methods and procedures for affixing bones and providing and creating a compressive effect on the bones are provided. Example methods include providing two bone ends or segments in approximation; providing a bone staple comprising a crown portion and an engagement portion, the engagement portion comprising a plurality of legs extending therefrom, the plurality of legs comprising bevels formed at the ends thereof; placing the bone staple against the bone ends or segments in approximation whereby the bevels of the legs are generally adjacent the bone of the bone ends or segments; and driving the legs within the bone of the bone ends or segments, the legs generally symmetrically diverging outwardly such that the bone of the bone ends or segments is compressed and thereby securing the bone ends or segments together in approximation.

According to another example embodiment, the present invention relates to a method of performing a surgical operation comprising preparing a bone for fusion or repair; stabilizing the bones with a pin, a clamp, a screw or by one or more hands; providing a sizer; bringing the sizer against the bones to be fixed and centering the sizer relative thereto; determining the appropriate size of a bone staple to be used to secure the bones together based on the size of the sizer relative to the size of the bones; providing a drill template; placing the drill template in the appropriate position relative to the bones and forming pilot holes; providing a bone staple comprising a crown portion and an engagement portion, the engagement portion comprising a radial array of legs of alternating length; and impacting the staple to cause engagement of the staple with the bones, thereby fully inserting the legs into the bones. Optionally, one or more specific openings formed on the crown portion and corresponding legs on the engagement portion are identified, and a wire loop is placed around the legs and through one or more of the openings. In one form, the wire is tensioned as desired to create compression, and then further optionally, a central screw is provided and placed within a central opening of the crown portion and tightened within the bone. Alternatively, the bone screw is placed within the central opening and tightened within the bone and then the wire is tensioned as desired to create compression. Further optional, prior to insertion of the bone staple into the bones, the wire can be tensioned to cause bending of one or more of the legs and then the bone staple with one or more of the legs being bent from the tensioned wire can be inserted into the bones. Furthermore, the bone screw can optionally be placed within the central opening of the crown portion and fastened to the bones.

While the invention has been described with reference to preferred and example embodiments, it will be understood by those skilled in the art that a variety of modifications, additions and deletions are within the scope of the invention, as defined by the following claims.

What is claimed is:

1. A bone staple comprising:
   a crown portion comprising a central opening defining a central axis of the bone staple, and a plurality of peripheral openings spaced from the central opening; and
   a plurality of legs extending from the crown portion, wherein at least one of the plurality of legs comprises an obliquely inclined bevel forming a sharp tip at a distal end portion thereof, the bevel facing inward toward the central axis of the bone staple,
   wherein the obliquely inclined bevel is configured to cause at least one of the plurality of legs to diverge outwardly from the central axis autonomously as the bone staple is implanted; and
   an articulation wire passing through the plurality of peripheral openings and engaging a plurality of the leas to define a tension band for providing compression to the plurality of engaged legs, thereby being adapted to provide a poly-axial compressive effect to underlying bone which is configured to be engaged with the bone staple.

2. The bone staple of claim 1, wherein at least one of the plurality of legs comprises a first length and at least another one of the plurality of legs comprises a different second length.

3. The bone staple of claim 2, wherein the first and second lengths of the legs comprise a ratio L1:L2 of about 2:1.

4. The bone staple of claim 2, comprising ten legs extending therefrom, five of the legs having the first length and five of the legs having the second length, wherein the legs alternate between the first length and the second length circumferentially around the crown portion.

5. The bone staple of claim 1, wherein each of the plurality of legs comprises an obliquely inclined bevel forming a sharp tip at a distal end portion thereof, the bevels facing inward toward the central axis of the bone staple, wherein the obliquely inclined bevels are configured to cause each of the plurality of legs to diverge outwardly from the central axis as the bone staple is implanted to create a poly-axial compressive effect to underlying bone segments as the staple is driven into the bone.

6. The bone staple of claim 5, wherein the diverging of the plurality of legs is configured to apply a symmetric compressive force to bone engaged with the bone staple as the staple is implanted.

7. The bone staple of claim 1, further comprising a screw configured for extending through the central opening.

8. A bone staple comprising a crown and a plurality of legs extending from the crown, wherein at least one of the plurality of leas has a first length, and at least one other of the plurality of legs has a second length different from the first length, the first length being at least about two times the second length, wherein each of the plurality of leas comprises an obliquely inclined bevel forming a sharp tip at a distal end portion thereof, the obliquely inclined bevels facing inward toward a central axis of the bone staple, wherein the obliquely inclined bevels are configured to cause the plurality of leas to diverge outwardly from the central axis as the bone staple is implanted and apply a symmetric compressive force to bone engaged with the bone staple;
   wherein the crown comprises a central opening and a plurality of peripheral openings spaced from the central opening, and wherein at least one articulation wire is passed through the plurality of openings and engages a plurality of the legs to define a tension band, the tension band providing compression to the plurality of engaged legs, thereby being adapted to provide a poly-axial compressive effect to underlying bone which is configured to be engaged with the bone staple.

9. The bone staple of claim 8, wherein the crown is generally circular and defines a diameter of between about 8 millimeters to about 26 millimeters.

10. The bone staple of claim 9, wherein the diameter of the crown is between about 12 millimeters to about 20 millimeters.

11. The bone staple of claim 8, wherein the plurality of legs alternate circumferentially about the crown between the first length and the second length.

12. A bone staple assembly comprising:
   a crown portion comprising a central opening defining a central axis, and a plurality of peripheral openings spaced from the central opening; and
   a plurality of legs extending from the crown portion, wherein at least one of the plurality of legs comprises an obliquely inclined bevel forming a sharp tip at a distal end portion thereof, the bevel facing inwardly toward the central axis of the bone staple; and
  an articulation wire passing through the plurality of peripheral openings and engaging a plurality of the legs to define a tension band for applying compressive force on the plurality of engaged legs when the articulation wire is tensioned, thereby being adapted to provide a compressive force to bone which is configured to be engaged with the bone staple.

* * * * *